(12) United States Patent
Hossack et al.

(10) Patent No.: US 6,171,248 B1
(45) Date of Patent: Jan. 9, 2001

(54) ULTRASONIC PROBE, SYSTEM AND METHOD FOR TWO-DIMENSIONAL IMAGING OR THREE-DIMENSIONAL RECONSTRUCTION

(75) Inventors: John A. Hossack; John W. Eaton, both of Palo Alto, CA (US)

(73) Assignee: Acuson Corporation, Mountain View, CA (US)

(*) Notice: Under 35 U.S.C. 154(b), the term of this patent shall be extended for 0 days.

(21) Appl. No.: 09/291,829

(22) Filed: Apr. 14, 1999

Related U.S. Application Data (62) Division of application No. 08/807,384, filed on Feb. 27, 1997.

(51) Int. Cl.⁷ ..................................................... A61B 8/00
(52) U.S. Cl. ............................................ 600/459; 600/447
(58) Field of Search ...................................... 600/447, 455, 600/443, 459, 460, 461

(56) References Cited

U.S. PATENT DOCUMENTS

| | | |
|---|---|---|
| Re. 30,397 | 9/1980 | King . |
| 3,888,238 | 6/1975 | Meindl et al. . |
| 4,140,022 | 2/1979 | Maslak . |
| 4,219,811 | 8/1980 | Herman et al. . |
| 4,241,608 | 12/1980 | Dees et al. . |
| 4,244,026 | 1/1981 | Dickey, Jr. . |
| 4,397,775 | 6/1990 | Engeler et al. . |
| 4,635,293 | 1/1987 | Watanabe . |
| 4,841,977 | 6/1989 | Griffith et al. . |
| 4,917,097 | 4/1990 | Proudian et al. . |
| 4,937,775 | 6/1990 | Engeler et al. . |
| 4,947,852 | 8/1990 | Nassi et al. . |
| 4,972,199 | 11/1990 | Raghavan et al. . |
| 5,000,185 | 3/1991 | Yock . |
| 5,014,710 | 5/1991 | Maslak et al. . |
| 5,064,290 | 11/1991 | McMurtry et al. . |
| 5,070,879 | 12/1991 | Herres . |
| 5,081,993 | 1/1992 | Kitney et al. . |
| 5,103,129 | 4/1992 | Slayton et al. . |
| 5,107,844 | 4/1992 | Kani et al. . |
| 5,123,415 | 6/1992 | Daiple . |
| 5,127,409 | 7/1992 | Daigle . |
| 5,158,071 | 10/1992 | Umemura et al. . |
| 5,159,931 | 11/1992 | Pini . |
| 5,161,537 | 11/1992 | Hashimoto et al. . |
| 5,186,176 | 2/1993 | Hiki et al. . |
| 5,186,177 | 2/1993 | O'Donnell et al. . |
| 5,199,437 | 4/1993 | Langberg . |
| 5,211,176 | 5/1993 | Ishigure et al. . |
| 5,215,093 | 6/1993 | Miyazuki et al. . |
| 5,257,629 | 11/1993 | Kitney et al. . |
| 5,273,045 | 12/1993 | Chihara et al. . |
| 5,285,788 | 2/1994 | Arenson et al. . |
| 5,315,512 | 5/1994 | Roth . |
| 5,320,105 | 6/1994 | Bonnefous et al. . |

(List continued on next page.)

FOREIGN PATENT DOCUMENTS

| | | |
|---|---|---|
| WO 97/00482 | 1/1997 | (WO) . |
| WO 98/25509 | 6/1998 | (WO) . |

OTHER PUBLICATIONS

"The Next Generation: New Bi–plane and End–Array Transducers with Color Doppler Capabilities" *B&K Medical Brochure*, (date unknown) two pages.

(List continued on next page.)

\* cited by examiner

*Primary Examiner*—Marvin M. Lateef
*Assistant Examiner*—Maulin Patel
(74) *Attorney, Agent, or Firm*—Brinks, Hofer, Gilson & Lione (57) ABSTRACT

An ultrasonic probe that includes at least two ultrasonic arrays and allows three dimensional images to be constructed of the region examined by the probe in a precise and facile manner.

27 Claims, 7 Drawing Sheets

U.S. PATENT DOCUMENTS

| | | |
|---|---|---|
| 5,325,860 | 7/1994 | Seward et al. . |
| 5,327,895 | 7/1994 | Hashimoto et al. . |
| 5,343,867 | 9/1994 | Shankar . |
| 5,345,940 | 9/1994 | Seward et al. . |
| 5,349,262 | 9/1994 | Grenon et al. . |
| 5,353,354 | 10/1994 | Keller et al. . |
| 5,368,037 | 11/1994 | Eberle et al. . |
| 5,377,682 | 1/1995 | Ueno et al. . |
| 5,379,642 | 1/1995 | Reckwerdt et al. . |
| 5,381,067 | 1/1995 | Greenstein et al. . |
| 5,398,691 | 3/1995 | Martin et al. . |
| 5,402,793 | 4/1995 | Gruner et al. . |
| 5,435,311 | 7/1995 | Umemura et al. . |
| 5,456,259 | 10/1995 | Barlow et al. . |
| 5,469,851 | 11/1995 | Lipschutz . |
| 5,471,988 | 12/1995 | Fujio et al. . |
| 5,474,073 | 12/1995 | Schwartz et al. . |
| 5,487,388 | 1/1996 | Rello et al. . |
| 5,492,125 | 2/1996 | Kim et al. . |
| 5,497,776 | 3/1996 | Yamazahi et al. . |
| 5,503,153 | 4/1996 | Liu et al. . |
| 5,515,853 | 5/1996 | Smith et al. . |
| 5,517,537 | 5/1996 | Greene et al. . |
| 5,529,070 | 6/1996 | Augustine et al. . |
| 5,531,224 | 7/1996 | Ellis et al. . |
| 5,538,004 | 7/1996 | Bamber . |
| 5,558,091 | 9/1996 | Acker et al. . |
| 5,566,674 | 10/1996 | Weng . |
| 5,568,813 | 10/1996 | Dietrich et al. . |
| 5,570,691 | 11/1996 | Wright et al. . |
| 5,575,286 | 11/1996 | Weng et al. . |
| 5,575,290 | 11/1996 | Teo et al. . |
| 5,582,173 | 12/1996 | Li . |
| 5,590,659 | 1/1997 | Hamilton et al. . |
| 5,606,975 | 3/1997 | Liang et al. . |
| 5,608,849 | 3/1997 | King, Jr. . |
| 5,612,713 | 3/1997 | Bhuva et al. . |
| 5,655,535 | 8/1997 | Friemel et al. . |
| 5,699,805 | 12/1997 | Seward et al. . |
| 5,704,361 | 1/1998 | Seward et al. . |
| 5,713,363 | 2/1998 | Seward et al. . |
| 5,724,976 | 3/1998 | Mine et al. . |
| 5,724,978 | 3/1998 | Tenhoff . |
| 5,735,281 | 4/1998 | Rafter et al. . |
| 5,776,067 | 7/1998 | Kamada et al. . |
| 5,797,849 | 8/1998 | Veseig et al. . |
| 5,876,345 * | 3/1999 | Eaton et al. ......................... 600/466 |
| 5,891,039 | 4/1999 | Bonnefous et al. . |
| 5,899,861 | 5/1999 | Friemel et al. . |
| 6,045,508 * | 4/2000 | Hossack et al. ..................... 600/447 |

OTHER PUBLICATIONS

Detmer, Paul R. et al. "3D Ultrasonic Image Feature Localization Based on Magnetic Scanhead Tracking: In Vitro Calibration and Validation" *Ultrasound in Med. & Biol.*, 1994, vol. 20, No. 9, pp. 923–936.

Leotta, Daniel F. et al. "Three–Dimensional Ultrasound Imaging Using Multiple Magnetic Tracking Systems and Miniature Sensors".

Ramamurthy, Bhaskar S. et al., Potential and Limitations of Angle–Independent Flow Detection Algorithms Using Radio–Frequency and Detected Echo Signals *Ultrasonic Imaging* 1991, vol. 13, pp. 252–268.

Three–Dimensional Reconstruction of Human Coronary and Peripheral Arteries from Images Recorded During Two–Dimensional Intravascular Ultrasound Examination,K. Rosenfield, et al., Circulation vol. 84, No. 5, pp. 1938–1956, (1991).

A. Shaulov et al., "Biplane Phased Array for Ultrasound Medical Imaging," (1988), pp. 635–638.

Laurence N. Bohs et al., "A Novel Method for Angle Independent Ultrasonic Imaging of Blood Flow and Tissue Motion," (1991), pp. 280–286.

Timothy C. Hodges et al., "Ultrasonic Three–Dimensional Reconstruction: In Vitro and In Vivo Volume and Area Measurement," (1994), pp. 719–729.

Hugh A. McCann et al., "Multdimensional Ultrasonic Imaging for Cardiology," (1988), pp. 1063–1072.

Elizabeth O. Ofili et al., "Three–Dimensional and Four–Dimensional Echocardiography," (1994), pp. 669–675.

J. Souquet et al., "Transesphageal Phased Array for Imaging the Heart," (1982), pp. 707–712.

LSI Logic, Appendix 2, "L64720 Video Motion Estimation Processor (MEP)," 1 page.

ISO/IEC Standard (MPEG Video), "Introduction—Part 2: Video," (1991) pp. 5–9.

Shinichi Tamura et al., "Three–Dimensional Reconstruction of Echocardiograms Based on Orthogonal Sections," (1985) pp. 115–124.

Frederich Dohery, M.D. et al., "Sonoline® Elegra Ultrasound Imaging Platform and Extended Field of view XFOVυ Imaging," (1995), 4 pages.

M. Belohlavek et al., "Multidimensional Ultrasonic Visualization in Cardiology," (1992) pp. 1137–1145.

Dan Sapoznikov et al., "Left Ventricular Shape, Wall Thickness and Function Based on Three–Dimensional Reconstruction Echocardiography," pp. 195. 496–498.

N. Bom et al., "Early and Recent Intraluminal Ultrasound Devices," (1989) pp. 79–88.

U.S. Ser. No. 08/874,792 filed Jun. 12, 1997.

O'Donnell, M., et al., "Synthetic Phased Array Imaging of Coronary Arteries with an Intraluminal Array," IEEE Ultrasonics Symposium, pp. 1251–1254 (1995).

Gussenhoven, E. et al., "Displacement Sensing Device Enabling Accurate Documentation of Catheter Tip Position," Intravascular Ultrasound, pp. 157–166 (1993).

One page product brochure of Powerpace Enhancement Package, (date unknown).

Two page B&K Medical product brochure describing B&K 8558 transducer and B&K 8557 transducer, (date unknown).

Bon, N. et al., "Early & Recent Intraluminal Ultrasound Devices", Intul Jrnl of Cardiac Imaging 4:pp. 79–88 1989.

END VIEW

ULTRASONIC PROBE, SYSTEM AND METHOD FOR TWO-DIMENSIONAL IMAGING OR THREE-DIMENSIONAL RECONSTRUCTION

This application is a division of Ser. No. 08/807,384 filing date Feb. 27, 1997.

FIELD OF THE INVENTION

This invention relates to an ultrasonic probe, system and method for acquiring two-dimensional image information and relative positional information to allow subsequent three dimensional reconstruction utilizing an ultrasonic probe that has at least two ultrasonic transducer arrays mounted thereon which generate differing image formats.

BACKGROUND OF THE INVENTION

Probes that incorporate more than one transducer array are known. For example, a 1994 model of the Toshiba biplane endocavity transducer incorporates linear imaging elements and axial imaging elements to offer a choice of views without transducer repositioning. B&K Medical Model 8558 bi-plane imaging transducer incorporates a linear ultrasound array and a 110° convex ultrasound array to allow for switching from longitudinal to transverse imaging and vice versa. In addition, the Acuson ER7B endorectal biplane transducer integrates a 128 element radial phased array which provides 150° of radial phased array coverage with a separate longitudinal array of 128 elements. These known probes allow different two dimensional views to be obtained from the different arrays.

Attempts have been made to construct three-dimensional images using a probe with a linear array by collecting multiple two dimensional image data frames along with relative positional information among the image data frames so that these image frames could be subsequently assembled into a three dimensional volume to form the desired three dimensional reconstruction. The relative positional information was acquired by externally rotating the probe while trying to maintain angular control. Such manual techniques are slow and cumbersome and therefore have many drawbacks. Thus, these probes have not been successfully used to construct three dimensional images.

Thus, it is desirable to provide an ultrasonic probe that allows three dimensional images to be constructed of the region examined by the probe in a precise and facile manner.

SUMMARY OF THE INVENTION

According to a first aspect of the present invention there is provided a method for registering image information acquired from an interior region of a patient. The method includes the steps of:
 (a) inserting an ultrasonic probe having a body having a longitudinal axis, a circumference and a distal end region, a first ultrasound array disposed in the distal end region of the body and a second ultrasound array disposed in the distal end region of the body into a patient to image an interior region of the patient;
 (b) acquiring image data with the first ultrasound array;
 (c) acquiring tracking data with the second ultrasound array;
 (d) repeating steps (b) and (c) after moving the ultrasonic probe along a direction having a component of motion in the tracking plane;
 (e) automatically determining the component of motion based on a comparison of the tracking data acquired in steps (c) and (d); and
 (f) automatically using the component of motion determined in step (e) to register the first image information acquired in step (d) with the first image information acquired in step (b).

According to a second aspect of the present invention there is provided a method for registering image information acquired from an interior region of a patient. The method includes the steps of:
 (a) inserting an ultrasonic probe having a body having a longitudinal axis, a circumference and a distal end region, a first ultrasound array disposed in the distal region of the body and a second ultrasound array disposed around the circumference of the distal end region of the body into a patient to image an interior region of the patient;
 (b) acquiring first two-dimensional image data in an image plane with the first ultrasound array;
 (c) acquiring tracking data in a tracking plane oriented at a non-zero angle with respect to the image plane with the second ultrasound array;
 (d) repeating steps (b) and (c) after moving the ultrasonic probe along a direction having a component of motion in the tracking plane;
 (e) automatically determining the component of motion based on a comparison of the tracking data acquired in steps (c) and (d); and
 (f) automatically using the component of motion determined in step (e) to register the first image information acquired in step (d) with the first image information acquired in step (b).

According to a third aspect of the present invention there is provided a probe including a body having a longitudinal axis, a circumference, and a distal end region; a linear phased array disposed in the distal end region of the body; and a radial phased array disposed 360° around the circumference of the body.

According to a fourth aspect of the present invention there is provided a system including a probe having a body having a longitudinal axis, a circumference, and a distal end region, a linear phased array disposed in the distal end region of the body, and a radial phased array disposed 360° around the circumference of the body; and a transmit beamformer and a receive beamformer coupled to each of the linear phased array and the first radial phased array.

DETAILED DESCRIPTION OF THE PRESENTLY PREFERRED EMBODIMENTS

Figure 1:
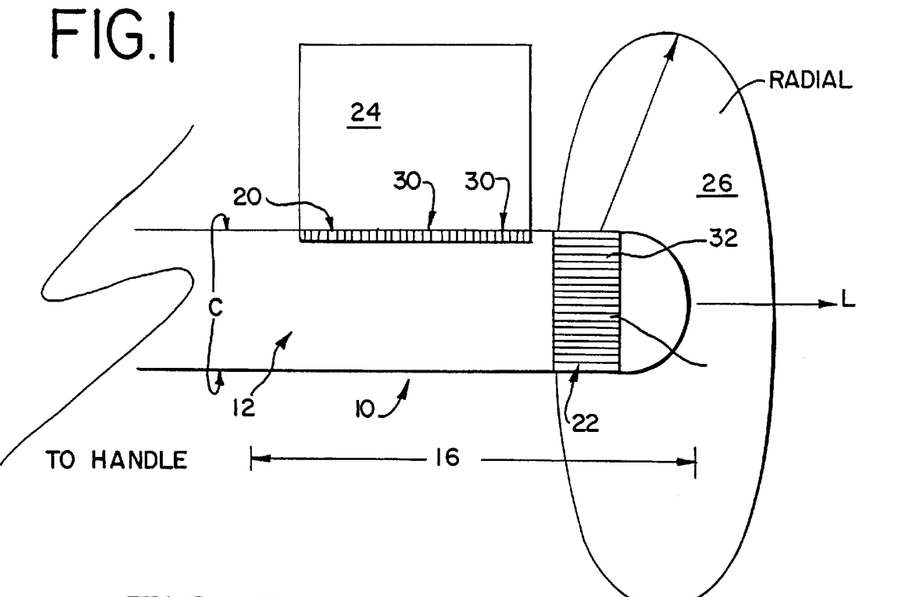
FIG. 1 is a schematic view of the distal portion of a probe according to a preferred embodiment of the present invention.

FIG. 1 is a schematic view of a distal portion of a probe 10 that includes a body 12, which preferably is in the form of a rigid shaft having a longitudinal axis L and a circumference C. The body 12 has a distal end region 18 which includes at least two ultrasonic transducer arrays that generate different image formats when excited as will be described in greater detail hereinafter. The probe 10 may have various configurations for various uses. For example, the probe 10 may be an endorectal probe, an endovaginal probe or a transesophageal probe. The particular shape of the probe 10 will be dictated by its use and FIG. 1 is merely intended to represent the distal end portion of the probe 10 which typically is a cylindrical shaft. The present invention, however, is not limited to such a configuration. A lens or acoustic window (not shown) may cover the emitting faces of the transducer arrays, however, it has not been shown for clarity purposes.

In a preferred embodiment, the body 12 is preferably constructed of RADEL™ available from Amoco Polymers of Atlanta, Ga. Other high impact thermoplastics preferentially having substantial chemical resistance may be used. The body 12 preferably has a length ranging from about 10 cm to about 20 cm and a diameter ranging from about 10 mm to about 20 mm.

A first ultrasonic transducer array 20 ("first array 20") and a second ultrasonic transducer array 22 ("second array 22") are provided in the distal end region 18 of the probe 10. In a preferred embodiment, the first array 20 is a linear phased array and the second array 22 is a radial phased array. In a preferred embodiment, the radial phased array is an annular array. When the annular array 22 is excited all of the emitted acoustic lines have a common origin lying at the center of the annular array 22. An annular array 22 is used to obtain a 360 degree scan. A 360 degree scan, however, is not always necessary for every application. In particular, in another preferred embodiment shown in FIG. 2 the radial array 22' may be formed by a curved linear phased array which does not form an entire annulus and only provides a partial radial scan. In another preferred embodiment shown in FIG. 3, the radial array 22" may be formed by a substantially planar linear phased array which provides a partial radial scan. A radial array, as that term is used in the present invention, is any array that generates a scan in a plane perpendicular to the longitudinal axis L of the probe when the array is excited. If the radial array is formed by a linear or curved linear phased array the scan obtained may be linear, sector or VECTOR™ format. A particular example is the Acuson V510B bi-plane transesophagael probe which includes two planar linear phased arrays operated in a VECTOR™ format to collect longitudinal and radial plane image data. The linear phased array 20 generates a sector, VECTOR™, or linear format image plane 24 upon excitation as illustrated in FIG. 1.

Linear phased array 20 is formed by a plurality of ultrasonic transducer elements 30 that are sequentially arranged along the longitudinal axis L of the body 12. The azimuth of the array 20 extends parallel with the longitudinal axis L of the body 12. In a preferred embodiment, the linear phased array 20 is formed by 128 transducer elements having an elevation dimension extending into the FIGS. 1–3 of about 5 mm and are spaced on a 0.3 or 0.4 mm pitch. The linear phased array 20 can be of conventional form, such as a flat linear phased array with a cylindrical elevation focusing lens. Alternately, the array 20 can be generally flat, but the transducer elements can be curved in elevation to focus. In this case, a non-refractive filler such as a polyurethane can be used since a focusing lens is no longer required. All imaging modes including B mode, color Doppler, color Doppler energy and the like are supported. The linear phased array 20 may include more or less than 128 elements and may have a different pitch and elevation.

Radial phased ultrasonic transducer array 22 in FIG. 1 is formed by a plurality of transducer elements 32 sequentially arranged circumferentially so that it is preferably concentric with the circumference of the body 12. In a preferred embodiment, the radial phased array 22 is formed by 128 elements having an elevation dimension of 5 mm spaced on a 0.2 mm pitch. In another preferred embodiment, the radial phased array 22 is formed by 256 elements having an elevation dimension of 5 mm spaced on a 0.25 mm pitch to form an annulus and provide a 360° scan. The annular array may be formed by wrapping a flat transducer array that has been partially diced into a circle around a support. Alternatively, the radial phased array 22 may be formed by fewer elements and, thus, provide less than a 360° scan. Of course, if the radial phased array 22 has the format shown in FIG. 2 or 3, the number of elements, pitch, and elevation may be different.

Figure 2:
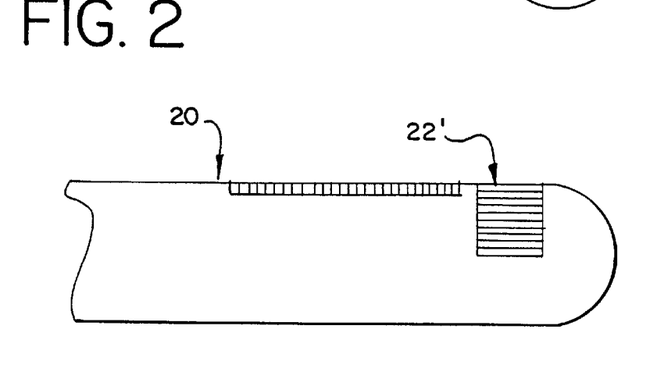
FIG. 2 is a schematic view of a distal portion of a probe according to another preferred embodiment of the present invention.
Figure 3:
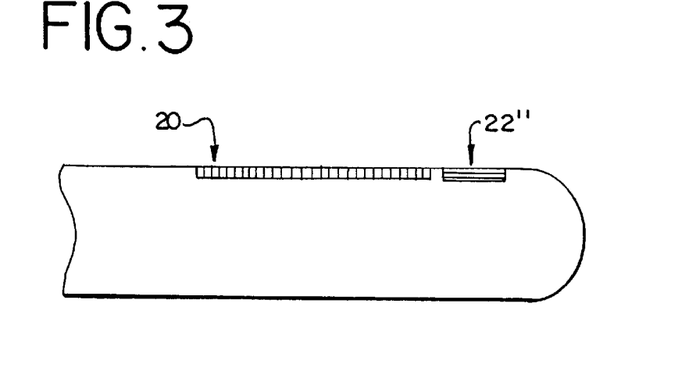
FIG. 3 is a schematic view of a distal portion of a probe according to still another preferred embodiment of the present invention.

As is well known in the art, conventional ultrasound transducers are typically constructed of piezoelectric material, such as PZT. In a preferred embodiment, the piezoelectric material for arrays 20 and 22 is preferably 3203HD sold by Motorola Ceramics of Albuquerque, N. Mex. Preferably, each transducer element includes two matching layers. The matching layer adjacent to the PZT is an epoxy loaded with alumina or lithium aluminum silicate and/or metal power such as tungsten preferably 325 mesh and possesses an acoustic impedance of approximately 8–10 MRayls. The second matching layer—further from the PZT—is preferably an unfilled epoxy possessing an impedance of approximately 2.5 MRayls. The arrays 20 and 22 are constructed using well known techniques which involve laminating the matching layers, an electroded slab of PZT and a flexible circuit onto a thin backing block substrate. Since a very high acoustic loss is desired, it may be preferable to form the backing block from polymeric particles which have been fused to form a macroscopically rigid structure having remnant tortuous permeability, as described in U.S. Pat. No. 5,297,553, assigned to the assignee of this invention. Once the structure has been laminated, individual elements are defined by dicing through the matching layers, PZT and partially into the backing block as is well known. Thereafter, the substrate can be bent to its final shape.

The ultrasonic probe 10 according to the preferred embodiments shown in FIGS. 1–3 can be used to reconstruct three dimensional images. More particularly, in a preferred embodiment, one array is used as an imaging array and the other array is used as a tracking array. For example, if the radial phased array 22, 22', 22" is used as the imaging array and the linear phased array 20 is used as the tracking array, multiple two dimensional image data sets are accumulated from the radial phased array as the probe is pushed or pulled through a region of interest. The linear phased array is used for collecting frame-to-frame tracking data by feature tracking between successive frames using, for example, the sum of absolute differences technique. In this way, the longitudinal displacement between successive radial phased scans is obtained and sufficient locating data is acquired to allow the multiple two dimensional image data sets to be assembled into a three dimensional volume. Alternatively, if the linear phased array 20 is used as the imaging array and the radial phased array 22, 22', 22" is used as the tracking array, multiple two dimensional image data sets are acquired using the linear phased array. The probe is rotated and the radial phased array acquires multiple data sets which are analyzed to determine the extent of rotation between frames. This provides enough locating information to allow the multiple two dimensional image data sets to be assembled into a three dimensional volume. Alternatively, both arrays 20 and 22 may be used as tracking arrays. Image reconstruction techniques are described in greater detail in U.S. patent application Ser. No. 08/807,498, entitled "Multiple Ultrasound Image Registration System, Method and Transducer," concurrently filed herewith which is a continuation-in-part of U.S. patent application Ser. No. 08/621,561, filed Mar. 25, 1996, which is a continuation-in-part of provisional patent application Serial No. 60/012, 578 filed Feb. 29, 1996, all of which are assigned to the assignee of the present invention and all of which are hereby incorporated herein by reference.

Figure 4:
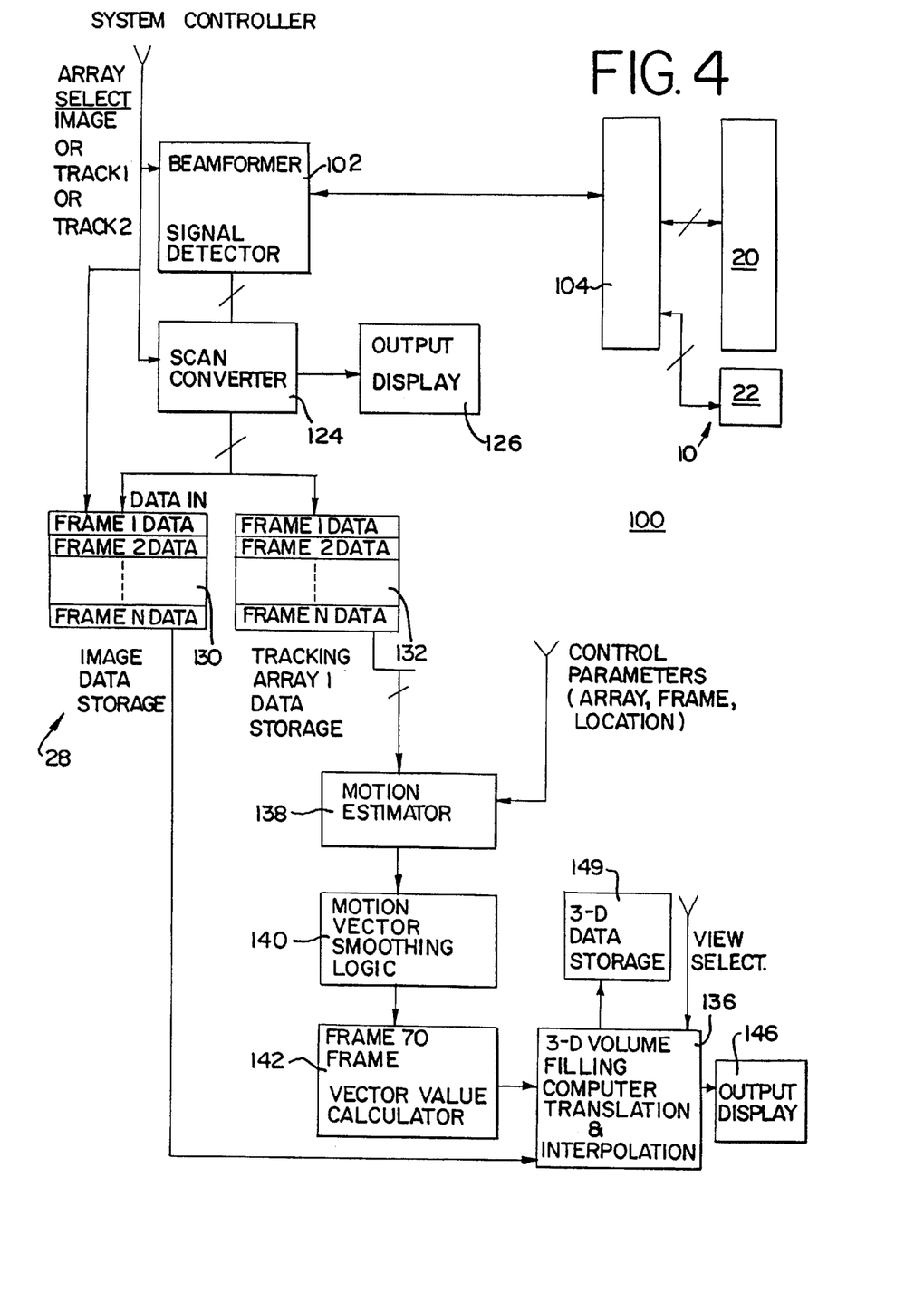
FIG. 4 is a block diagram of an ultrasonic imaging system according to a presently preferred embodiment of the present invention.

FIG. 4 is a block diagram of an ultrasonic imaging system according to a preferred embodiment of the present invention. The following discussion will first present a system overview, and then a detailed description of select components of the system.

System Overview

The system 100 includes a beamformer system/signal detector 102 which includes both transmit and receive beamformers and is connected via a multiplexer/demultiplexer 104 to an ultrasonic probe 10 such as that shown in FIG. 1. If both arrays are operating in a conventional mode where the active transducer aperture is operated simultaneously in a phased manner, then any conventional device—such as the Acuson XP may be used for element 102. If the arrays are being operated in a synthetic aperture mode, i.e., in which the elements of the array are operated in a sequential rather than simultaneous mode, then it is necessary for the system to store the receive element signals in a temporary store until all of the transmit-receive element combinations have been received. Once all the echo signals have been received then the data in the temporary storage registers are delayed and summed to produce a beamformed signal. Systems for implementing this type of synthetic focusing by temporarily storing single channel data until all channel data has been received are well known, for example, see Proudian U.S. Pat. No. 4,917,097. The system preferably accumulates multiple signals for each transmitter-receiver pair so that signal averaging is achieved thereby resulting in an improvement in the signal to noise ratio. Alternatively, instead of using a common transducer element for both transmitter and receiver a separate receiver can be used for each transmitter channel selected. Such a method is described by O'Donnell et al. in "Synthetic Phased Array Imaging of Coronary Arteries With An Intraluminal Array," Proceedings of the 1995 IEEE Ultrasonics Symposium, pp. 1251–1254 (1995). Individual elements are sequentially used as transmitters. As each element is used as a transmitter, separate adjacent elements are used as receivers on a sequential basis. In this way, the array can be made to synthesize the operation of a conventional large scale phased array scanner but with the added advantage that dynamic transmit focusing as well as dynamic receive focusing is possible since the individual channel transmit path lengths are known uniquely. The low signal to noise ratio of the array elements is partially overcome by averaging the successive firings of the same element pairs. Preferably, as many averages as possible are used consistent with not providing an imaging frame rate which is slower than desired by the user. Preferably the array is operated with frequencies in the range of about 5 to 10 MHz. If lower frequencies are used, then the linear array has less problems with grating lobes. Alternatively, a lower frequency can be used when operating steered ultrasonic lines as describe in U.S. Pat. No. 5,549,111. When the linear phased array is used to accumulate tracking information, the array can be operated at a high frequency, for example, 10 MHz, since only a relatively small set of data is required in order to derive the motion information.

The beamformer system/signal detector 102 sends excitation signal pulses to the arrays 20 and 22 and supplies summed returning echoes to a signal detector 102. The beamformer system/signal detector 102 accumulates data from the array elements 20 and 22 and forms beamformed acoustic line outputs. The output of the beamformer signal detector 102 is supplied to a scan converter 124. The scan converter 124 controls an output display 126 to display preferably the two images generated by the two arrays 20, 22. In a preferred embodiment, the output display 126 displays the views obtained from the linear phased array 20 and the radial phased array 22 simultaneously on a split screen. Alternatively, the operator may flip back and forth between views. Other display options will be described in greater detail hereinafter.

In addition, scan-converted image information from the scan converter 124 is stored in a data storage system 128. In this preferred embodiment, the data storage system 128 includes two separate storage arrays 130 and 132, each storing data for image frames from a respective one of the arrays 20 and 22. In a preferred embodiment, one array of the probe is used for collecting image data that will be used to construct displayed representation of the region of interest and other array operates as a tracking array. In a preferred embodiment, the linear phased array 20 is used to collect image data and the radial phased array 22 is use to collect tracking data. Thus, image information from the image array 20 is stored as frames of image data in the storage array 130, and tracking information from the tracking array 22 is stored as respective frames of tracking data in the storage array 132. The frames of data in the storage arrays 130 and 132 are all time marked, so that they can be associated with one another appropriately. This time marking can take the form of real-time clock information or frame number information, for example.

The frames of image data in the storage array 130 are applied to a computer 136. It is these frames that are used to form the displayed representation of the region of interest. The tracking frames stored in storage array 132 are not necessarily registered to create a displayed reconstruction of the region of interest but are instead used to determine the relative positions of individual frames of image data from the image data storage array 130.

In order to estimate movement of the probe 10 between successive frames of the image data, the tracking information from the tracking array data storage array 132 is supplied to a motion estimator 138. The motion estimator 138 compares sequences of frame data from the tracking array 22 to estimate a component of motion of the probe 10 between the respective frames. This estimate of the component of motion is smoothed in logic 140, and then applied to a calculator 142 that calculates a vector value defining the best estimate of the movement between selected frames of the data stored in the image data storage array 130. This vector is then applied as another input to the computer 136.

The computer 136 registers selected frames of image data from the image data storage array 130 with respect to one another by appropriate use of the vectors supplied by the calculator 142. Also, any necessary interpolation is done, and the respective frames of image data are stored in proper registration with respect to one another in a three-dimensional data storage device 144. The computer 136, when operating in a display mode, can select appropriate information from the three-dimensional data storage device 144 to provide a desired image on the display 146. For example, cross sections can be taken in various planes, including a wide variety of planes that do not correspond to the planes of the image data. Also, surface renderings and segmentation displays can be created if desired.

Common signal conductors can be used between the beamformer/signal detector 102 and the housing for the probe 10. In the housing, individual signals are routed between the signal conductors and the transducer elements of the arrays 20 and 22 by high voltage analog switches or multiplexers.

Figure 5:
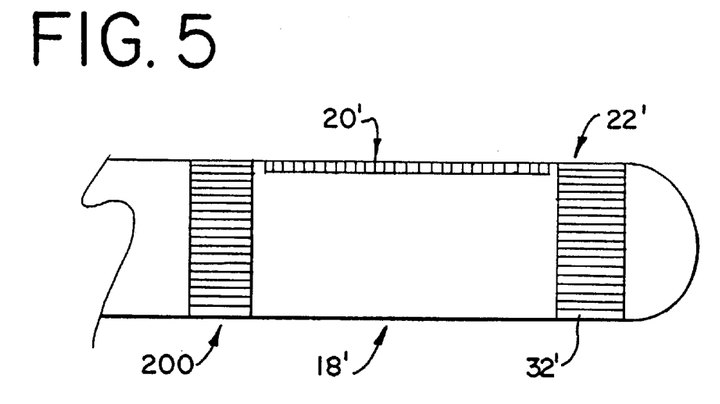
FIG. 5 illustrates the distal end region of an ultrasonic probe according to another preferred embodiment of the present invention.
Figure 6:
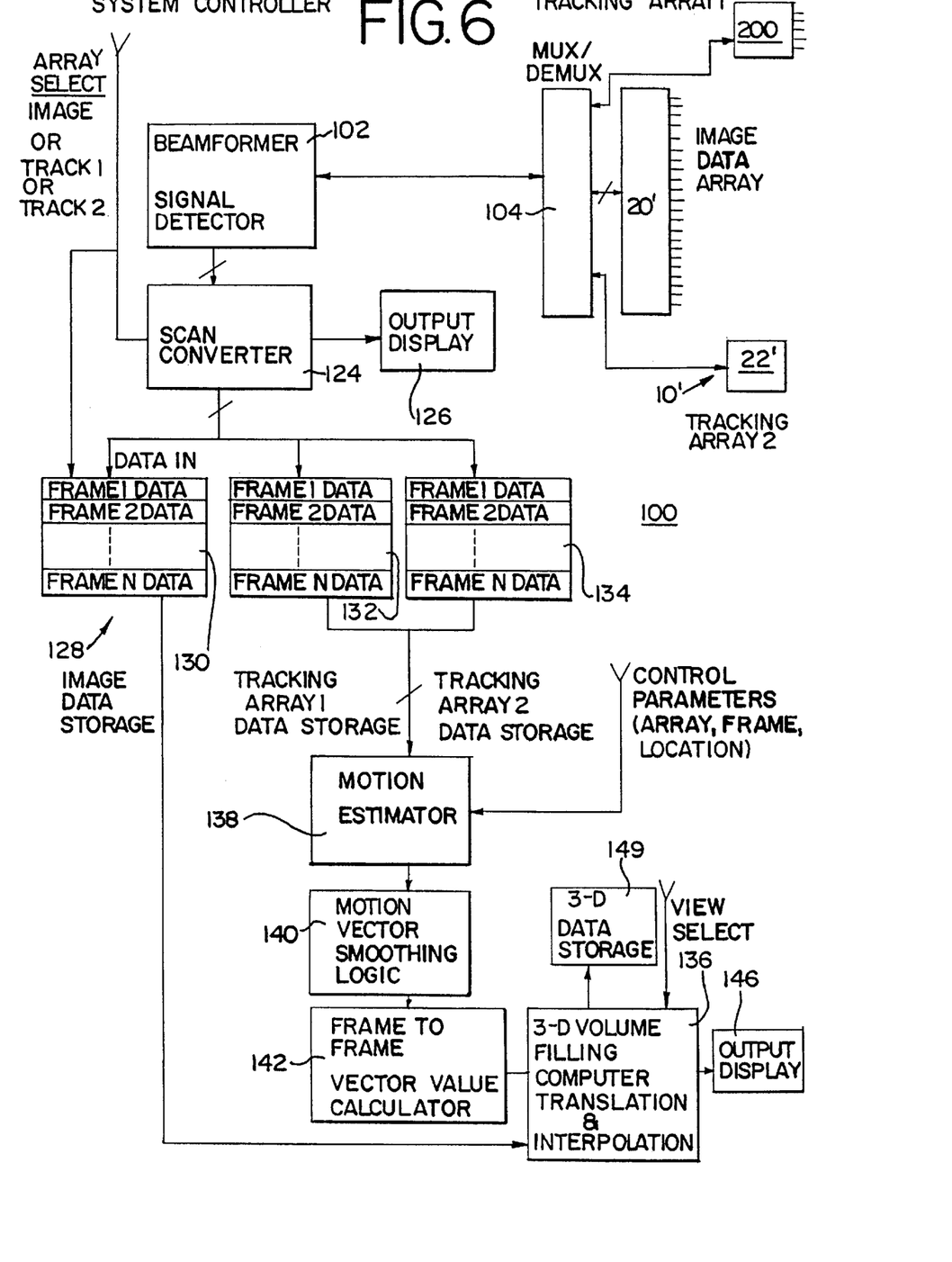
FIG. 6 is a block diagram of an ultrasonic imaging system according to a preferred embodiment of the present invention.
Figure 7:
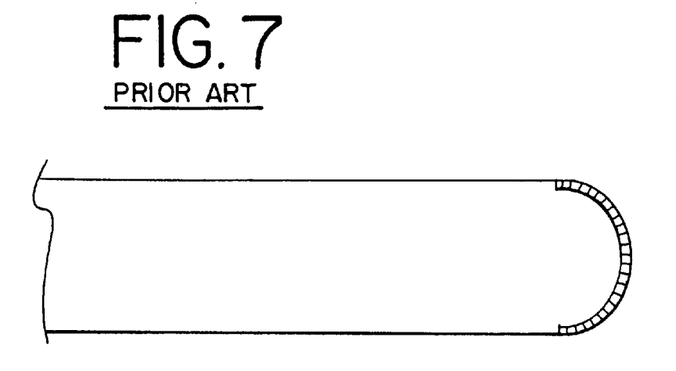
FIGS. 7 and 7A illustrate the distal end region of a prior art probe.
Figure 7A:
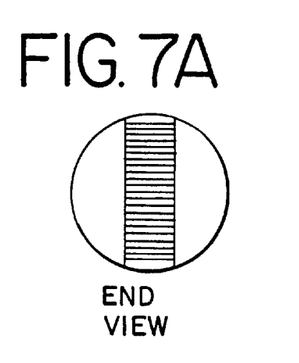
Figure 8:
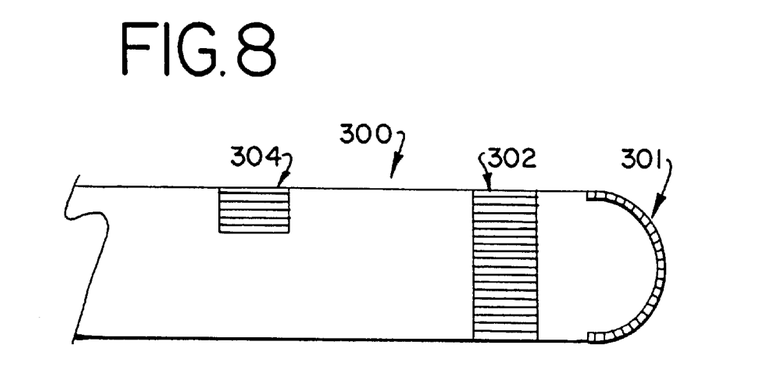
FIG. 8 illustrates the distal end region of an ultrasonic probe according to a preferred embodiment of the present invention.

Various other preferred embodiments of transducer probes are possible and within the scope of the present invention. FIG. 5 illustrates the distal end region 18' of an ultrasonic probe according to another preferred embodiment of the present invention. In this preferred embodiment, a second tracking array 200, preferably a radial phased array, is provided proximal of the linear phased array 20'. FIG. 6 illustrates a system in which a second tracking array 200 is incorporated in the probe. As previously described with respect to radial array 22, the second tracking array 200 may extend around the entire circumference to obtain a 360° scan of the probe or it may extend only partial around the circumference. When two tracking arrays are used, the ability to compensate for impure rotation (where one or both ends of the image array 20' is linearly translated as well as rotated) is substantially increased. Since the tracking arrays are on either side of the image array, and the exact geometry of the image data plane with respect to the tracking arrays is known, it is possible to interpolate linearly along the image data array azimuth axis to calculate the exact pixel translations for all points on the image data plane. FIG. 7 illustrates the distal end region of an endo vaginal (EV) or endo rectal (ER) probe according to the prior art. A tightly curved linear array is provided at the end of the cylindrical probe as shown in end view in FIG. 7A. FIG. 8 illustrates the distal end region of an EV or ER probe according to a preferred embodiment of the present invention. The probe 300 has a tightly curved array similar to that shown in FIG. 7 but also includes an imaging array 301 at the distal end of the probe except that a first tracking array 302 and optionally a second tracking array 304 have been added to the probe 300 to facilitate three dimensional reconstruction. In a preferred embodiment, array 301 at the distal end of the probe is used as the imaging array and the first and second arrays 302 and 304 are used as tracking arrays. The first tracking array 302 extends 360 degrees around the shaft of the probe while the second tracking array 304 extend only partially around the shaft of the probe. Either or both of the tracking arrays may scan 360° or less than 360°. In use, the probe is inserted into the rectum or vagina and is rotated so that the image array 301 sweeps out a volume and the first and second tracking arrays 302 and 304 track motion within a plane. While a second tracking array 304 is shown, the probe may be provided with only one imaging array and one tracking array. By providing the second tracking array, impure rotation of the probe can be accounted for as previously discussed. In the preferred embodiment shown in FIG. 8, the first tracking array 302 proximal of the imaging array 301 is preferably set back a distance of 10 mm and, if a second tracking array 304 is provided, it is set back about 3 or 4 cm proximal of the first tracking array 302.

Figure 9:
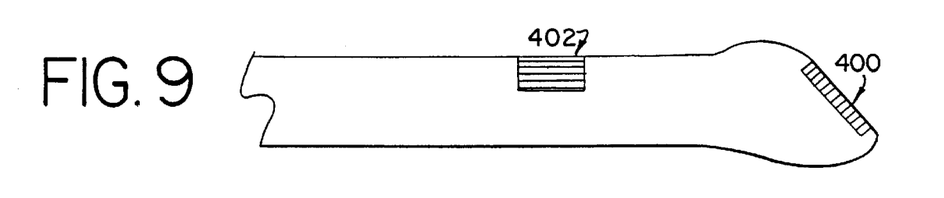
FIG. 9 illustrates the distal end region of an ultrasonic probe according to a preferred embodiment of the present invention.

Other preferred embodiments may be provided. For example, the Acuson EV7, shown diagrammatically in FIG. 9, which has a phased array 400 mounted at the distal end of the probe at an angle of about 60 degrees with respect to the end of the cylindrical base of the probe and may be modified to include at least one tracking array 402 located in the side of the probe, for example, to permit motion tracking as the probe is rotated and the image array at the end of the probe sweeps out a volume.

Figure 10:
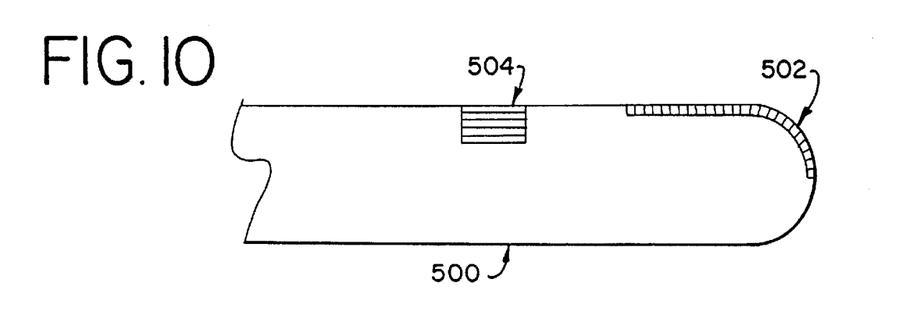
FIG. 10 illustrates the distal end region of an ultrasonic probe according to a preferred embodiment of the present invention.

Another preferred embodiment of a probe according to the present invention is shown in FIG. 10. In this embodiment, the probe 500 includes an imaging array 502 in the distal end of the probe and at least one tracking array 504 is provided on the side of the probe. The imaging array 502 is preferably a combined curved and flat array. With this design, the probe must be rotated 360 degrees in order to scan an entire volume whereas the probe shown in FIG. 8 only requires the probe to be rotated 180 degrees to scan an entire volume. This type of array may be simpler to manufacture since the number of elements contained within the end region is minimized and hence wiring to the elements is less cramped. The tracking arrays should form scans in the radial plane. Preferably the tracking arrays are radial in form and scan 360° although they do not absolutely have to be annular arrays.

Angular Motion Detection

Figure 11:
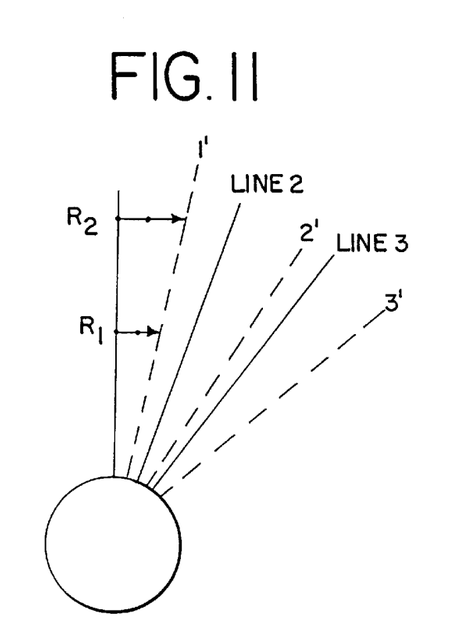
FIG. 11 illustrates a subset of beam data.
Figure 12:
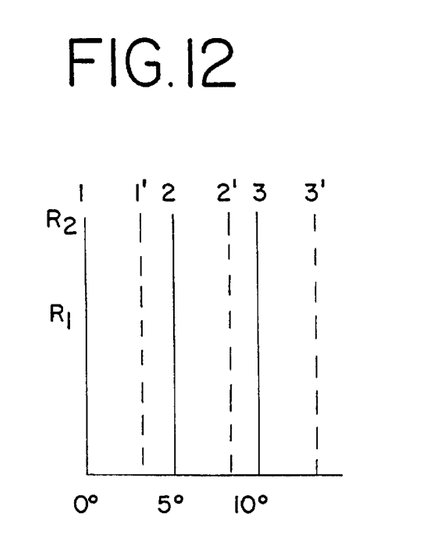
FIG. 12 illustrates the subset data shown in FIG. 11 unwrapped.

With respect to the radial arrays described previously, the output of the beamformer are polar in format. For measuring rotational motion rather than Cartesian motion, it is simpler to retain the acoustic line data in polar format, i.e., not scan converted. Typically, the beamformer outputs lines are detected to form unipolar signals and are scan converted to digital quantities. FIG. 11 illustrates how a subset of beam data appears in reality, i.e. scan converted into Cartesian coordinates. It is much simpler, however, to unwrap the axial display shown in FIG. 11, i.e. do not scan convert it. FIG. 12 illustrates how this data is unwrapped to form the straight polar case. The increment between successive beam lines is simply their angular separation, for example, 5 degrees. With respect to detecting the motion of pixel values from Line 1 to Line 1' etc., it is evident that by using polar coordinates the correct answer for rotation is arrived at more simply. In this case the lines are spaced 5 degrees apart and the detected motion from Line 1 to Line 1' is approximately two-thirds of 5 degrees.

Display Options

Since one is to able collect image data from both arrays and use one or both sets for tracking motion of the other plane described previously, various display options exist.

Figure 13:
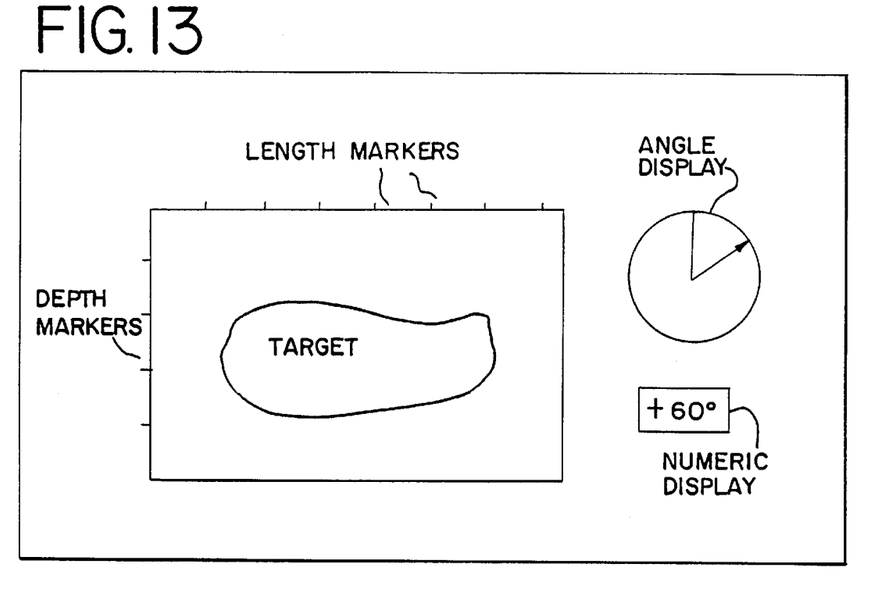
FIG. 13 illustrates a display generated by the linear phased array used with the present invention.

FIG. 13 illustrates a display generated by the linear phased array. The angle of probe rotation with respect to some user defined arbitrary starting point has been measured. This angle is an indication of the relative angular direction of the image frame produced by the linear phased array and may be displayed as a circular icon as shown in FIG. 13 and/or a numeric output as is also displayed. The circular icon assumes that the user defined origin is at the top of the circle (for example)and the angular rotation of the probe with respect to this position is shown by an arrow suitably angled with respect to the starting point, i.e., the top of the circle. Software for displaying such icons is well within the scope of those skilled in the art.

Figure 14:
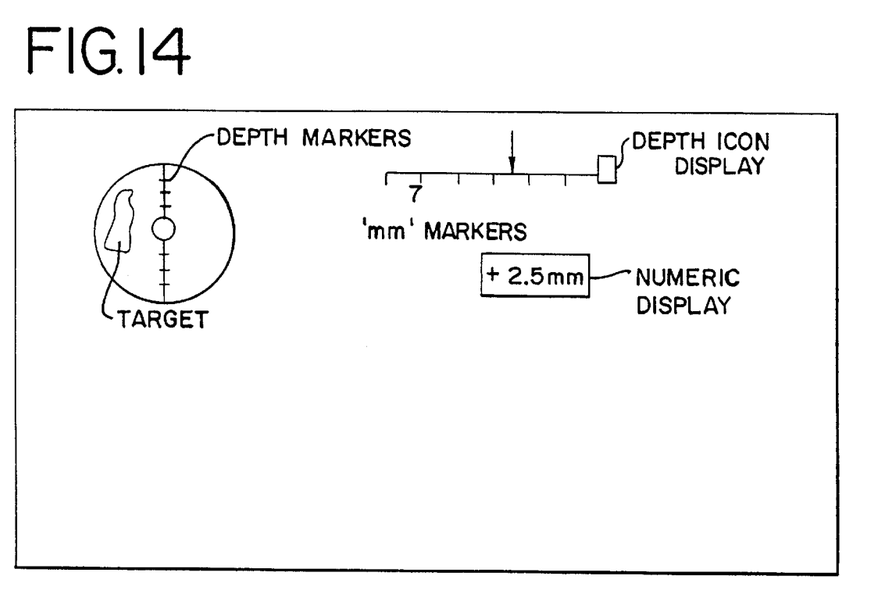
FIG. 14 illustrates a display generated by the radial phased array used with the present invention.

FIG. 14 illustrates a display generated by the radial phased array. The radial display is presented and depth of penetration as detected by motion sensed from the linear array is also displayed. Again, the reference point for the start of motion detection is arbitrary and the user should have the option of resetting it by, for example, selection of a key on a keyboard. An icon display for the detected depth relative to the last resetting of the depth measurement is also shown in FIG. 14. Preferably the icon is in the form of a ruler like object with an arrow pointing to the current position. Optionally, a numeric display indicating millimeters of penetration is also provided.

Figure 15:
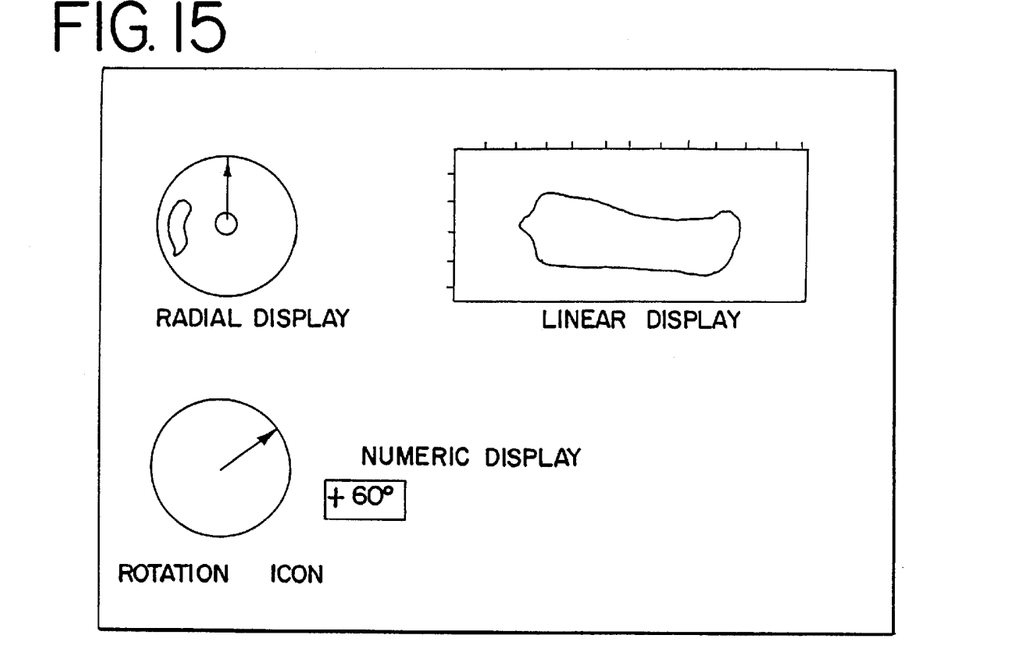
FIG. 15 illustrates a display generated by images formed by both the linear and radial phased arrays used with the present invention.

FIG. 15 illustrates a display of images formed both the linear phased array and the radial phased array. In the embodiment shown in FIG. 15, both the radial and linear array images are displayed each having tick marks indicating a scale in either mm or cm. Preferably, the scan converter sets the millimeter scales to be equal in dimension in both displays. Displaying multiple ultrasound images is relatively well known, for example, simultaneous B-Mode and M-Mode. In this case, an angle display is also provided which indicates the present position of the linear array image with respect to the last resetting of the angle measurement.

Figure 16:
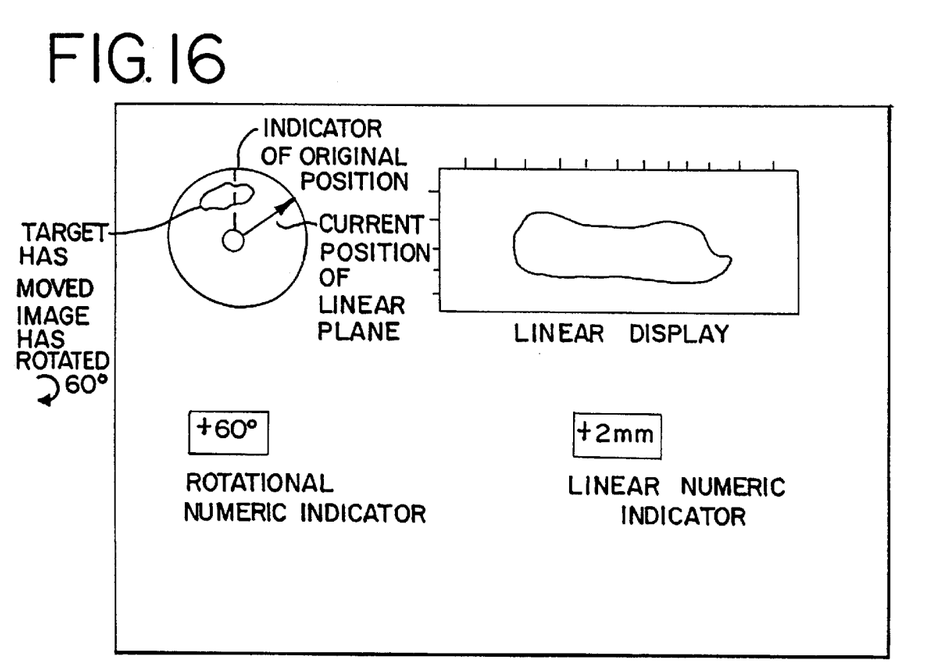
FIG. 16 illustrates a display generated by both the linear and radial phased arrays according to a preferred embodiment of the present invention.

FIG. 16 illustrates a display formed by both the linear phased array and the radial phased array. In this preferred embodiment, the radial image display is rotated according to the detected rotation angle such that the display rotation completely compensates for rotation of the physical device. Thus, the image appears to remain static though the image is moving with respect to the array. If the system detects that an arbitrary object has moved 20 degrees anticlockwise, the system signals the scan converter to rotate the image 20 degrees clockwise to compensate. The concept of the detecting image motion and altering the display to correct for it is described in considerable detail in Bamber U.S. Pat. No. 5,538,004.

If desired, the probe can include an absolute sensor incorporated in its distal end region for position, orientation, or both, such as a magnetic sensor or an accelerometer. The sensor 19 may be used to supplement or back up the motion detection approach and may be of the types described in Keller U.S. Pat. No. 5,353,354 or one of the smaller sensors manufactured by Biosense, Inc. of Setauket, N.Y.

While this invention has been shown and described in connection with the preferred embodiments, it is apparent that certain changes and modifications, in addition to those mentioned above, may be made from the basic features of the present invention. Accordingly, it is the intention of the Applicant to protect all variations and modifications within the true spirit and valid scope of the present invention.

What is claimed is:

1. A method for registering image information acquired from an interior region of a patient, said method comprising the steps of:

(a) inserting an ultrasonic probe into a patient to image an interior region of the patient, the ultrasonic probe having a body having a longitudinal axis, a circumference and a distal end region, a first ultrasound array disposed in the distal end region of the body and a second ultrasound array disposed in the distal end region of the body;

(b) acquiring a plurality of sets of image data with the first ultrasound array, the first ultrasound array moved between acquisition of at least some of the sets of image data;

(c) acquiring a plurality of sets of tracking data with the second ultrasound array, the second ultrasound array moved between acquisition of at least some of the sets of tracking data;

(d) automatically determining a component of motion based on a comparison of at least a portion of the tracking sets acquired in step (c); and (e) automatically using the component of motion determined in step to register select ones of the image data sets acquired in step (b).

2. A method according to claim 1 wherein the second ultrasound array is oriented to scan in a radial plane upon receiving an excitation signal.

3. A method according to claim 1 wherein the first ultrasound array is oriented to scan in a linear format upon receiving an excitation signal.

4. A method according to claim 1 wherein the first ultrasound array is oriented to scan in a sector format upon receiving an excitation signal.

5. A method according to claim 1 wherein the first ultrasound array is oriented to scan in a VECTOR™ format upon receiving an excitation signal.

6. A method according to claim 2 wherein the first ultrasound array is oriented to scan in a linear format upon receiving an excitation signal.

7. A method according to claim 2 wherein the first ultrasound array is oriented to scan in a sector format upon receiving an excitation signal.

8. A method according to claim 2 wherein the first ultrasound array is oriented to scan in a VECTOR™ format upon receiving an excitation signal.

9. The method of claim 1 wherein step (e) comprises the step of correlating the tracking data acquired in steps (c) and (d).

10. The method of claim 1 wherein the image data comprises information selected from the group consisting of B mode information, color Doppler velocity information, color Doppler energy information, and combinations thereof.

11. A method according to claim 1 wherein the first ultrasound array is a linear phased array.

12. A method according to claim 1 wherein the second ultrasound array is a radial phased array.

13. A method according to claim 1 wherein the first ultrasound array is a linear phased array and the second ultrasound array is a radial phased array.

14. A method according to claim 1 wherein the first ultrasound array is a radial phased array and the second ultrasound array is a linear phased array.

15. The method according to claim 1 wherein the step of moving the ultrasonic probe comprises rotating the ultrasonic probe about its longitudinal axis.

16. The method according to claim 1 wherein the step of moving the ultrasonic probe comprises translating the ultrasonic probe through a region of interest in a direction parallel with its longitudinal axis.

17. A method for registering image information acquired from an interior region of a patient, said method comprising the steps of:

(a) inserting an ultrasonic probe into a patient to image an interior region of the patient, the ultrasonic probe having a body having a longitudinal axis, a circumference and a distal end region, a first ultrasound array disposed in the distal region of the body and a second ultrasound array disposed in the distal end region of the body;

(b) acquiring a plurality of sets of two-dimensional image data in an image plane with the first ultrasound array, the first ultrasound array moved between acquisition of at least some of the sets of image data;

(c) acquiring a plurality of sets of tracking data in a tracking plane oriented at a non-zero angle with respect to the image plane with the second ultrasound array, the second ultrasound array moved between acquisition of at least some of the sets of tracking data;

(d) automatically determining a component of motion based on a comparison of at least a portion of the tracking sets acquired in step (c); and (e) automatically using the component of motion determined in step to register select ones of the image data sets acquired in step (b).

18. The method according to claim 17 wherein the step of moving the first and second ultrasound arrays comprises translating the ultrasonic probe in a direction parallel to the longitudinal axis.

19. The method of claim 17 further comprising the steps of:

(f) repeating steps (b), (c)and (d) and accumulating the component of motion detected in step (d) to generate composite detected motion wherein the composite detected motion indicates the motion of the ultrasonic probe with respect to a predetermined reference point;

(g) displaying the two-dimensional image data acquired in step (b); and (h) displaying the composite detected motion determined in step (d).

20. The method according to claim 19 wherein the step of displaying the composite detected of motion comprises displaying an icon representation of the composite detected motion.

21. The method according to claim 20 wherein the second array is a radial phased array and the icon is a circle with an arrow indicating the degree of rotation.

22. The method according to claim 20 wherein the second array is a linear phased array and the icon is a ruler with an arrow indicating the degree of translation.

23. The method according to claim 19 further comprising the step of (i) acquiring two-dimensional image data in the tracking plane with the second array; and (j) displaying at least a portion of the two-dimensional image information acquired in step (i).

24. The method according to claim 23 wherein the step of displaying the composite detected motion comprises displaying an icon representative of the composite detected motion.

25. The method to claim 24 wherein the icon is displayed over the two-dimensional image data displayed in step (j).

26. The method according to claim 19 wherein the step of displaying the composite detected motion comprises displaying a numerical value representative of the composite detected motion.

27. A method for imaging an interior region of a patient, the method comprising the steps of:

(a) inserting an ultrasonic probe having a body having a longitudinal axis, a circumference, and a distal end region, a linear phased array disposed in the distal end region of the body and a radial phased array disposed 360° around the circumference of the body into a patient to image an interior region of the patient;

(b) operating the linear phased array to image a first region during a first period of time; and (c) operating the radial phased array to image a second region during a second period of time.

* * * * *